US009603931B2

(12) United States Patent
Yi et al.

(10) Patent No.: US 9,603,931 B2
(45) Date of Patent: Mar. 28, 2017

(54) MACROMOLECULE FOR DELIVERING PROTEIN, POLYPEPTIDE OR PEPTIDE DRUGS AND A PRODUCTION METHOD FOR THE SAME, AND A SLOW RELEASE COMPOSITION FOR PROTEIN, POLYPEPTIDE OR PEPTIDE DRUGS AND A PRODUCTION METHOD FOR THE SAME

(75) Inventors: Yil Woong Yi, Daejeon (KR); Min Hyo Seo, Daejeon (KR); Bong Oh Kim, Daejeon (KR); In Ja Choi, Daejeon (KR); Hye Jeong Yoon, Daejeon (KR); Se Yoon Kim, Seoul (KR); Sang Jun Lee, Daejeon (KR); Joong Woong Cho, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 122 days.

(21) Appl. No.: 13/519,729

(22) PCT Filed: Dec. 28, 2010

(86) PCT No.: PCT/KR2010/009421
§ 371 (c)(1),
(2), (4) Date: Jun. 28, 2012

(87) PCT Pub. No.: WO2011/081406
PCT Pub. Date: Jul. 7, 2011

(65) Prior Publication Data
US 2013/0274188 A1 Oct. 17, 2013

(30) Foreign Application Priority Data
Dec. 29, 2009 (KR) .................. 10-2009-0132861

(51) Int. Cl.
| A61K 47/34 | (2006.01) |
| C07C 67/465 | (2006.01) |
| C07C 69/68 | (2006.01) |
| C08G 63/06 | (2006.01) |
| C08G 63/91 | (2006.01) |
| C08J 3/215 | (2006.01) |

(52) U.S. Cl.
CPC ............ *A61K 47/34* (2013.01); *C07C 67/465* (2013.01); *C07C 69/68* (2013.01); *C08G 63/06* (2013.01); *C08G 63/912* (2013.01); *C08J 3/215* (2013.01); *C08J 2367/04* (2013.01)

(58) Field of Classification Search
CPC ...... A61K 47/34; C08G 63/06; C08G 63/912; C08J 3/215; C08J 2367/04; C07C 67/465; C07C 69/68
See application file for complete search history.

(56) References Cited

U.S. PATENT DOCUMENTS

| 5,514,380 | A | 5/1996 | Song et al. |
| 5,668,288 | A * | 9/1997 | Storey et al. .................. 546/257 |
| 6,221,958 | B1 * | 4/2001 | Shalaby et al. .............. 525/54.1 |
| 6,541,033 | B1 | 4/2003 | Shah |
| 2004/0247561 | A1 | 12/2004 | Seo et al. |
| 2004/0253195 | A1 * | 12/2004 | Seo et al. .................... 424/70.11 |
| 2010/0286075 | A1 | 11/2010 | Lee et al. |

FOREIGN PATENT DOCUMENTS

| EP | 1 647 567 A1 | 4/2006 |
| JP | 859642 A | 1/1961 |
| JP | 63-69825 A | 3/1988 |
| JP | 7-309938 A | 11/1995 |
| JP | 62-135521 A | 6/1997 |
| JP | 2000-509084 A | 7/2000 |
| JP | 2002-535426 A | 10/2002 |
| JP | 2003-26606 A | 1/2003 |
| KR | 10-0517253 B1 | 9/2005 |
| KR | 10-2009-0073970 A | 7/2009 |
| WO | WO 94/15587 A2 | 7/1994 |
| WO | WO 97/38975 A1 | 10/1997 |
| WO | WO 97/39738 A2 | 10/1997 |
| WO | WO 98/27980 A2 | 7/1998 |
| WO | WO 00/43435 A1 | 7/2000 |
| WO | WO 2005/107813 A1 | 11/2005 |
| WO | WO 2006/014067 A1 | 2/2006 |

OTHER PUBLICATIONS

Kiran et al., "Lipase-catalysed polymerization of lactic acid and its film forming properties", World Journal of Microbiology & Biotechnology, vol. 19, 2003, pp. 859-865.
International Search Report for PCT/KR2010/009421 dated Sep. 28, 2011.

* cited by examiner

Primary Examiner — Suzanne Ziska
Assistant Examiner — Thurman Wheeler
(74) Attorney, Agent, or Firm — Birch, Stewart, Kolasch & Birch, LLP

(57) ABSTRACT

The present invention relates to a macromolecule for delivering protein, polypeptide or peptide drugs and to a production method for the same, as well as to a slow release composition for protein, polypeptide or peptide drugs comprising the same, and more specifically relates to a polylactic acid derivative compound of Chemical formula 1 of which the numerical average molecular weight is no more than 7000 daltons and to a production method for the same, as well as to a slow release composition for protein, polypeptide or peptide drugs using the same and to a production method for the same.

5 Claims, 7 Drawing Sheets

MACROMOLECULE FOR DELIVERING PROTEIN, POLYPEPTIDE OR PEPTIDE DRUGS AND A PRODUCTION METHOD FOR THE SAME, AND A SLOW RELEASE COMPOSITION FOR PROTEIN, POLYPEPTIDE OR PEPTIDE DRUGS AND A PRODUCTION METHOD FOR THE SAME

TECHNICAL FIELD

The present invention relates to a polymer for protein, polypeptide or peptide drug delivery, a method for preparing the polymer, a composition comprising the polymer for sustained release of protein, polypeptide or peptide drug, and a method for preparing the composition. More specifically, the present invention relates to a polylactic acid derivative compound of the following chemical formula 1 having a number average molecular weight of no more than 7,000 daltons and its preparation method, and a sustained release composition of protein, polypeptide or peptide drug and its preparation method using the same:

[Chemical Formula 1]

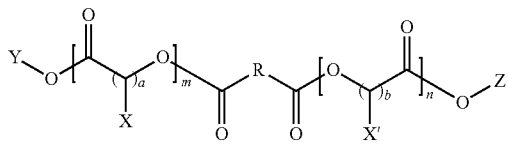

In the above chemical formula 1, X, X', Y, Z, R, m, n, a and b are the same as defined herein.

BACKGROUND ART

As the technology in the field of genetic engineering has rapidly progressed, the functions and roles of proteins and peptides have been identified and their mass production has become possible. As a consequence, many protein or peptide drugs have been commercially available, and the effort to develop new drugs by utilizing them has been continuously made.

When proteins or peptides are orally administered, it is difficult for them to pass through the intestine wall and they would be readily degenerated or decomposed by enzymes in the digestive canal, thereby providing very low bioavailability. Therefore, they are developed as a form of injectable formulation.

In case of an injectable formulation, in order to resolve patients' inconvenience due to frequent administration, various methods have been attempted to develop sustained release formulations, which can continuously provide the pharmacological effect for a long period only by a single administration. Such attempts have been disclosed in many references (Khaled Al-Tahami et al., "Smart Polymer Based Delivery Systems for Peptides and Proteins", Recent Patents on Drug Delivery & Formulation 2007, Vol. 1, No. 1, pp. 65-71, 2007; Fei Wu et al., "Polymer-Based Sustained-Release Dosage Forms for Protein Drugs, Challenges, and Recent Advances", AAPS Pharm Sci Tech, Vol. 9, No. 4, pp. 1 1218-1229, 2008).

Commercially available sustained release protein preparations include the products produced by applying PEGylation technology—which conjugates polyethylene glycol (PEG) with proteins—to interferon (PEGasys®, PEGintron®), GCSF (Neulasta®), asparaginase (Oncaspar®), adenosine deaminase (Adagen®), etc. However, as conjugates of PEGs having the molecular weight of 5,000 to 50,000 daltons with proteins, they are novel compounds and thus the verification of their biological safety and effectiveness is necessarily required in order for application to other proteins. Furthermore, high cost is required for their production.

In addition, sustained release preparations for peptide drugs such as leuprolide acetate (Lupron® Depot), octreotide (Sandostatin®), goserelin acetate (Zoladex®), triptorelin pamoate (Trelatar® Depot), etc. have been commercialized by using polylactic acid or polylactic acid-glycolic acid polymer—which are biodegradable polymers—as a microparticle delivery carrier. However, their effects of sustained release are still unsatisfactory.

For protein drugs, only the sustained release formulation of human growth hormone (Nutropin® Depot) has acquired the approval from USFDA. However, it was completely withdrawn from the market in 2004 because of its insufficient effect as compared with daily administration formulations.

As such, the formulations utilizing polylactic acid or polylactic acid-glycolic acid polymer microparticles for protein or peptide drug as developed up to date still have the problems such as initial burst and insufficient sustained release effect that are to be solved as sustained release formulations. Furthermore, economical factors including production cost increase due to the denaturation and big loss of drug during the production process are also the problems involved in such formulations.

DETAILED DESCRIPTION

Technical Purpose

The present invention is to solve the problems involved in the prior arts as stated above. The technical purpose of the present invention is to provide a polymer which has good sustained release effect of drug without the problems of initial burst and toxicity and thus is particularly suitable for sustained release delivery of protein, polypeptide or peptide drug, and to provide a sustained release composition for protein, polypeptide or peptide drug comprising the same as a drug delivery carrier.

In another aspect, the technical purpose of the present invention is to provide a method for efficiently preparing the sustained release composition according to the present invention without using an organic solvent.

Technical Solution

To achieve the above-mentioned technical purposes, the present invention provides a polylactic acid derivative compound of the following chemical formula 1 having a number average molecular weight of no more than 7,000 daltons:

[Chemical Formula 1]

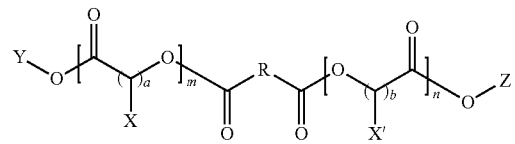

In the above chemical formula 1,

X and X' are independently hydrogen, alkyl or aryl,

Y and Z are independently absent or an alkali metal, m and n are independently an integer of 0 to 95, provided that 5<m+n<100, a and b are independently an integer of 1 to 6, R is unsubstituted or substituted —(CH$_2$)$_k$— where k is an integer of 0 to 10, a divalent alkenyl having 2 to 10 carbon atoms, a divalent aryl having 6 to 20 carbon atoms, or a combination thereof.

The expression "Y and Z are independently absent" used herein means that the oxygen independently connected to Y and Z is in the form having a negative charge, i.e. the form of $^-$O—.

In another aspect, the present invention provides a method for preparing a polylactic acid derivative compound of the following chemical formula 2, the method comprising the steps of: 1) polymerizing lactic acid or its derivative in the form of a free acid or a lactone with a dicarboxylic acid to obtain a polylactic acid derivative having carboxylic acids on both ends; and 2) dissolving the polylactic acid derivative obtained in the above step 1) in an organic solvent, and adding an aqueous solution of alkali metal salt to the resulting solution to obtain a salt of the polylactic acid derivative:

[Chemical Formula 2]

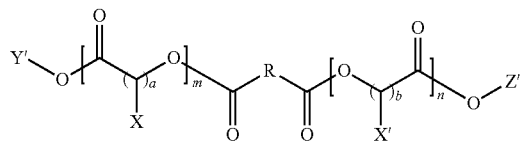

In the above chemical formula 2, X, X', R, m, n, a and b are the same as defined herein, and Y' and Z' are independently an alkali metal.

In another aspect, the present invention provides a complex of the polylactic acid derivative compound of the chemical formula 1 having a number average molecular weight of no more than 7,000 daltons, with a multivalent metal ion; and a sustained release composition comprising the same.

In another aspect, the present invention provides a sustained release composition of protein, polypeptide or peptide drug, comprising: i) a protein, polypeptide or peptide as an active ingredient, ii) the polylactic acid derivative compound of the chemical formula 1 as a drug delivery carrier, and iii) a multivalent metal ion.

In another aspect, the present invention provides a sustained release composition of protein, polypeptide or peptide drug, comprising: i) a protein, polypeptide or peptide as an active ingredient, and ii) a complex of the polylactic acid derivative compound of the chemical formula 1 with a multivalent metal ion, as a drug delivery carrier. This sustained release composition comprises microparticles in which the active ingredient such as protein, polypeptide or peptide is entrapped within the complex formed from the polylactic acid derivative compound of the chemical formula 1 and the multivalent metal ion.

In another aspect, the present invention provides a method for preparing a sustained release composition of protein, polypeptide or peptide drug, the method comprising the steps of: a) preparing an aqueous solution containing i) a protein, polypeptide or peptide as an active ingredient, and ii) the polylactic acid derivative compound of the chemical formula 1; and b) adding the aqueous solution of the above step a) dropwise to an aqueous solution comprising multivalent metal ion to obtain a precipitate.

Advantageous Effects

The sustained release drug delivery composition utilizing the polymer according to the present invention facilitates the sustained release of active ingredient such as protein, polypeptide or peptide. In addition, since the method for preparing said composition does not use any organic solvent, the denaturation of drugs during the production process can be prevented and thus the pharmacological effect of the drug can be maximized. In addition, no separate procedure for removing an organic solvent is required. Furthermore, since 90% or more of inclusion efficiency of protein, polypeptide or peptide drug can be achieved, the loss of drug during the production process can be minimized.

MODE FOR INVENTION

Figure 1:
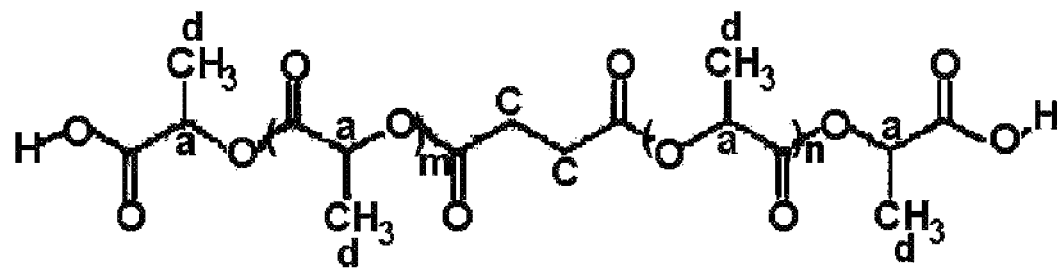
FIG. 1 is a $^1$H-NMR spectrum obtained from the polylactic acid derivative compound prepared in Preparation Example 1, dissolved in CDCl$_3$.
Figure 1:
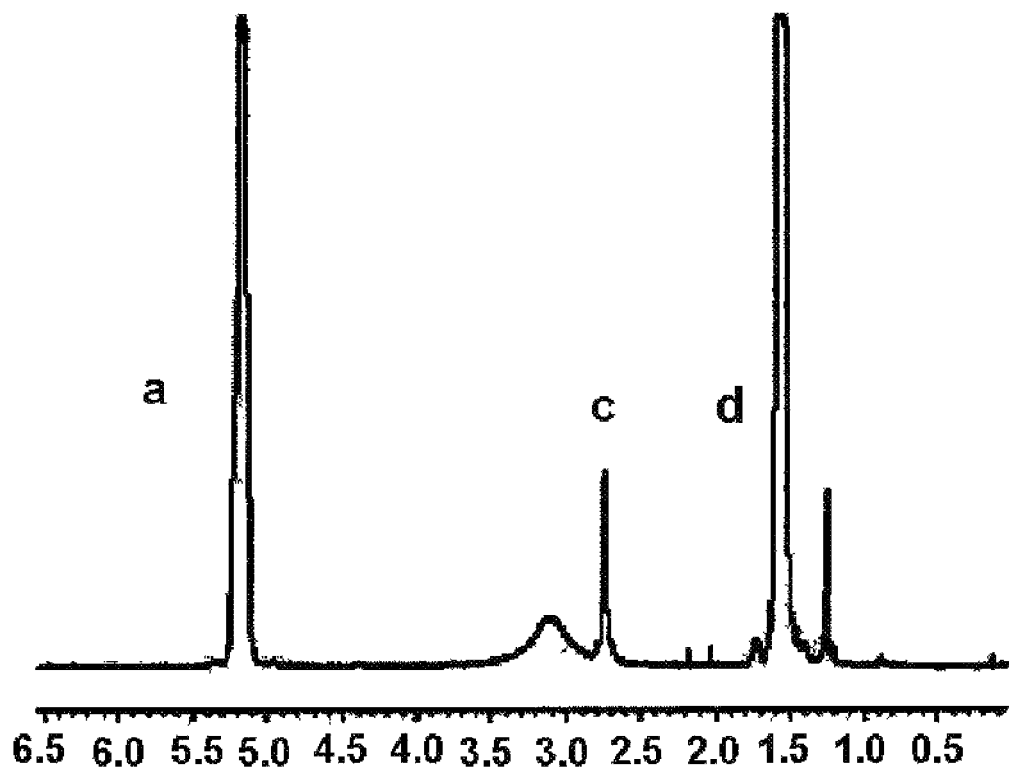

Hereinafter, the present invention will be described more specifically.

1. Polylactic Acid Derivative Compound and Method for Preparing the Same

The polylactic acid derivative compound for sustained release delivery of protein, polypeptide or peptide drug, as provided according to the present invention, has carboxylic groups on both ends and is represented by the following chemical formula 1:

[Chemical Formula 1]

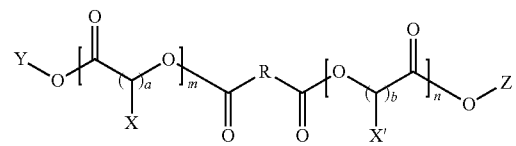

In the above chemical formula 1,

X and X' are independently hydrogen, alkyl or aryl,

Y and Z are independently absent or an alkali metal, m and n are independently an integer of 0 to 95, provided that 5<m+n<100, a and b are independently an integer of 1 to 6, R is unsubstituted or substituted —$(CH_2)_k$— where k is an integer of 0 to 10, a divalent alkenyl having 2 to 10 carbon atoms, a divalent aryl having 6 to 20 carbon atoms, or a combination thereof.

The expression "Y and Z are independently absent" above means that the oxygen independently connected to Y and Z is in the form having a negative charge, i.e. the form of $^-O$—.

According to an embodiment of the present invention, in the above chemical formula 1, X and X' are independently hydrogen, alkyl having 1 to 4 carbon atoms, or aryl having 6 carbon atoms and being unsubstituted or substituted with alkyl having 1 to 4 carbon atoms. More specifically, X and X' are independently hydrogen, methyl or phenyl, and still more particularly, they are methyl.

According to an embodiment of the present invention, in the above chemical formula 1, Y and Z are independently absent or an alkali metal. In case of Y and Z being an alkali metal, concretely the compound can be represented by the chemical formula 2. In case of Y and Z being absent, it means that both ends of the polymer compound of the chemical formula 1 are present in the form of anion, and concretely the compound can be represented by the chemical formula 3. Specifically, the alkali metal can be independently sodium, potassium or lithium.

[Chemical Formula 2]

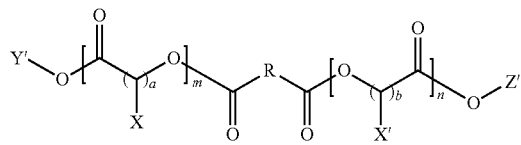

In the above chemical formula 2, X, X', R, m, n, a and b are the same as defined herein, and Y' and Z' are independently an alkali metal.

[Chemical Formula 3]

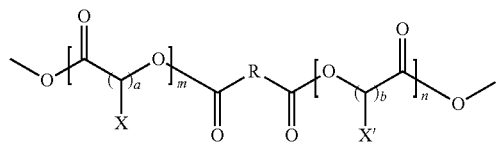

In the above chemical formula 3, X, X', R, m, n, a and b are the same as defined herein; and according to an embodiment of the present invention, R is —$(CH_2)_k$— where k is an integer of 0 to 10.

In the above chemical formula 1, when R is a divalent alkenyl having 2 to 10 carbon atoms or a divalent aryl having 6 to 20 carbon atoms, they can also be independently substituted with hydroxy group or C1-C5 alkyl.

In the above chemical formula 1, m and n preferably satisfy the requirement of 10<m+n≤70.

According to a preferred embodiment of the present invention, the polylactic acid derivative compound is represented by the following chemical formula 4:

[Chemical Formula 4]

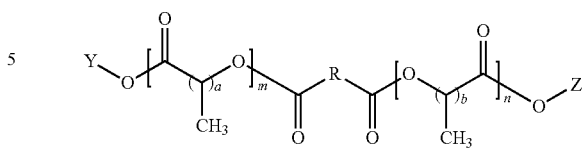

In the above chemical formula 4, Y, Z, R, m, n, a and b are the same as defined herein.

The polylactic acid derivative compound of the chemical formula 1 according to the present invention is water-soluble, and has a number average molecular weight of no more than 7,000 daltons, preferably 500 to 7,000 daltons, more preferably 700 to 5,000 daltons, and still more preferably 1,000 to 4,000 daltons. If the number average molecular weight is greater than 7,000 daltons, the polylactic acid derivative compound is not dissolved in water, and thus is not suitable for use as a drug delivery carrier. In addition, if the number average molecular weight is below 500 daltons, the molecular weight is small and the compound may be decomposed in body too rapidly, and thus it may be difficult to expect the sustained release of drug.

The polylactic acid derivative compound of the present invention comprises two blocks, for example, selected from the group consisting of polylactic acid, polylactide, polyglycolide, polymandelic acid, polycaprolactone and a copolymer thereof, with a center of dicarboxylic acid. According to an example of the present invention, the polylactic acid derivative compound comprises two blocks selected from the group consisting of polylactic acid, a copolymer of lactic acid and mandelic acid, a copolymer of lactic acid and glycolic acid, and a copolymer of lactic acid and caprolactone. More particularly, the polylactic acid derivative compound comprises two blocks of polylactic acid.

Dicarboxylic acid having 3 to 10 carbon atoms such as oxalic acid, malonic acid, malic acid, succinic acid, glutaric acid, adipic acid, pimelic acid, suberic acid, azelaic acid, sebacic acid, dodecanedioic acid, or a mixture thereof can be preferably used as the dicarboxylic acid. In addition, C4-C12 unsaturated dicarboxylic acid such as fumaric acid or maleic acid, C8-22 aryl dicarboxylic acid such as phthalic acid or terephthalic acid can also be used.

In the polylactic acid derivative compound of the chemical formula 1 according to the present invention, both ends are ionic and thus may or may not form ionic bond with alkali metal ion, as specifically represented by the chemical formulas 2 and 3, respectively. The anions of said ends can act to form the ionic binding complex through either direct bonding to multivalent metal ion, or in case of alkali metal ion, substitution with multivalent metal ion.

In another aspect, the present invention provides a method for preparing a polylactic acid derivative compound of the chemical formula 2, the method comprising the steps of: 1) polymerizing lactic acid or its derivative in the form of a free acid or a lactone with a dicarboxylic acid to obtain a polylactic acid derivative having carboxylic acids on both ends; and 2) dissolving the polylactic acid derivative obtained in the above step 1) in an organic solvent, and adding an aqueous solution of alkali metal salt to the resulting solution to obtain a salt of the polylactic acid derivative.

For example, in step 1) of the method for preparing the polylactic acid derivative compound of the present invention, said lactic acid or its derivative in the form of a free acid or a lactone—which can be used as a monomer—may be selected from the group consisting of lactic acid, lactide, glycolide, mandelic acid, caprolactone, and mixtures thereof.

The ratio of the used amounts between lactic acid or its derivative in the form of a free acid or a lactone and dicarboxylic acid is not particularly limited, and can be freely selected in the range within which the polylactic acid derivative compound of the chemical formula 1 can be obtained. According to an embodiment of the present invention, 1 to 20 parts by weight of dicarboxylic acid may be used with respect to 100 parts by weight of lactic acid or its derivative in the form of a free acid or a lactone.

More concretely, in step 1) of the method for preparing the polylactic acid derivative compound of the present invention, the polylactic acid derivative having carboxylic acids on both ends can be prepared by heating a mixture of monomers of lactic acid or its derivative in the form of a free acid or a lactone and dicarboxylic acid having 3 to 10 carbon atoms at 80° C. to 180° C., removing water for 0.5 to 4 hours, and then polymerizing the mixture at a temperature of 150 to 250° C. for 10 to 48 hours. In the above step of the production process, if the reaction temperature is below 150° C. or the reaction time is less than 10 hours during the polymerization after water removal, it may be difficult to obtain the polymer with the desired molecular weight. If the reaction temperature is higher than 250° C. or the reaction time exceeds 48 hours, there may be the problem of thermal decomposition of the polymer.

In step 2) of the method for preparing the polylactic acid derivative compound of the present invention, the polylactic acid derivative having carboxylic acids on both ends obtained in step 1) is dissolved in an organic solvent, and then an aqueous solution of alkali metal salt is added to the resulting solution to obtain the polylactic acid derivative compound of the chemical formula 2.

For example, the alkali metal can be selected from the group consisting of sodium bicarbonate, sodium carbonate, potassium bicarbonate, potassium carbonate, lithium carbonate and mixtures thereof. Concretely, sodium bicarbonate or potassium bicarbonate can be used. As the organic solvent, water-miscible organic solvents can be used. Concretely, acetonitrile or acetone can be used. In step 2), the ratio of the used amounts between the polylactic acid derivative having carboxylic acids on both ends and the alkali metal salt is not particularly limited, and can be freely selected in the range within which the polylactic acid derivative compound of the chemical formula 2 can be obtained. According to an embodiment of the present invention, 2 to 10 moles of the alkali metal salt can be used with respect to 1 mole of the polylactic acid derivative having carboxylic acids on both ends.

The method for preparing the polylactic acid derivative compound of the present invention can further comprise after step 2), the step of adding, for example, sodium chloride to the resulting polymer solution, and separating and recovering the organic layer, and then drying the recovered organic layer under vacuum to remove the organic solvent, thereby obtaining the polylactic acid derivative compound of the chemical formula 2.

2. Complex, Sustained Release Composition, and Method for Preparing the Same

In another aspect, the present invention provides a complex of the polylactic acid derivative compound of the chemical formula 1 having the number average molecular weight of no more than 7,000 daltons, with a multivalent metal ion. Said complex is useful as a drug delivery carrier.

The polylactic acid derivative compound of the chemical formula 1 according to the present invention is explained above, and has anionic ends. Therefore, the complex can be formed through ionic bonding between the multivalent metal ion and 2 moles or more of the polylactic acid derivative compound of the chemical formula 1. In the complex of the present invention, the multivalent metal ion can be a di- or trivalent metal ion, for example, a multivalent ion of a metal selected from the group consisting of zinc, calcium, magnesium and iron. For example, the multivalent metal ion can be provided in a form of salt compound such as chloride salts of those metals, but not specifically limited thereto.

According to an embodiment of the complex of the present invention, the polylactic acid derivative compound of the chemical formula 1 is the polylactic acid derivative compound of the chemical formula 3 as explained above.

In another aspect, the present invention provides a sustained release composition of protein, polypeptide or peptide drug, comprising: i) a protein, polypeptide or peptide as an active ingredient, ii) the polylactic acid derivative compound of the chemical formula 1 as a drug delivery carrier, and iii) a multivalent metal ion.

In another aspect, the present invention provides a sustained release composition of protein, polypeptide or peptide drug, comprising: i) a protein, polypeptide or peptide as an active ingredient, and ii) a complex of the polylactic acid derivative compound of the chemical formula 1 with a multivalent metal ion, as a drug delivery carrier.

According to an embodiment of the sustained release composition of the present invention, the complex can be formed through ionic bonding of the multivalent metal ion and 2 moles or more of the polylactic acid derivative compound of the chemical formula 1, and the complex can function as a drug delivery carrier. The active ingredient is entrapped therein to form microparticles.

According to an embodiment of the sustained release composition of the present invention, the polylactic acid derivative compound of the chemical formula 1 is the polylactic acid derivative compound of the chemical formula 3 as explained above.

In the sustained release composition of the present invention, the active ingredient is a protein, polypeptide or peptide. In case where any one of these terms is used alone herein, it should be understood to designate all of protein, polypeptide or peptide unless specifically mentioned.

The terms, "sustained release," "sustained release delivery" or "sustained release drug delivery" as used herein mean that a single administration of drug maintains the effective concentration of the drug in blood for a long period, for example, 72 hours or longer. Particularly, the general administration route of polypeptides is subcutaneous, intramuscular or intravenous injection, etc. but it is disadvantageous since frequent injections are required for effective treatment. Thus, the present invention seeks to develop and provide a sustained release delivery system for resolving any inconvenience due to such frequent administration.

In the sustained release composition of the present invention, the examples of the active ingredient can include growth hormone, erythropoietin, monoclonal antibody, granulocyte colony stimulating factor, macrophage colony stimulating factor, granulocyte-macrophage colony stimulating factor, thrombopoietin, insulin-like growth factor, epithelial growth factor, platelet-derived growth factor, fibroblast growth factor, transforming growth factor, interferon, interleukin, tumor necrosis factor, streptokinase, urokinase, staphylokinase, DNAse, glucocerebrosidase, alpha galactosidase, exenatide, octreotide, insulin, glucagon, luteinizing hormone releasing hormone, goserelin, leuprorelin, follicle stimulating factor, thyroid stimulating hormone, fertirelin, calcitonin, corticotropin releasing factor, brain natriuretic peptide, thymopentin, corticotropin, elcatonin, beta amyloid, triptorelin, buserelin, thymosin, somatostatin, alarelin, angiotensin, argipressin, atosiban, bivalirudin, cetrorelix, deslorelin, desmopressin, elcatonin, enfuvirtide, eptifibatide, GLP-1, gonandorelin, lyspressin, nafarelin, nesiritide, oxytocin, pramlintide, secretin, teriparatide, terlipressin, tetracosactide, vapreotide, and mixtures thereof.

In the sustained release composition of the present invention, the active ingredient can be used in an amount of 0.01 to 60 wt % (% by weight), more concretely 0.05 to 50 wt %, based on the dry weight of the sustained release composition of the present invention. If the content of the active ingredient is below 0.01 wt % of the dry weight of the sustained release composition, it may be difficult to obtain the intended pharmacological effect, whereas if the content is greater than 60 wt %, there may be a problem due to initial burst of the drug.

In the sustained release composition of the present invention, the polylactic acid derivative compound of the chemical formula 1 can be used such that it is included in an amount of 39.9 to 99.9 wt %, more concretely 50 to 99 wt %, based on the dry weight of the sustained release composition of the present invention. If the content of the polylactic acid derivative compound is below 39.9 wt % on the basis of the dry weight of the sustained release composition, the sustained release effect may not be obtained, whereas if the content is greater than 99.9 wt %, the dosage may exceed the possible maximum single dose to human body in a conventional manner.

In the sustained release composition of the present invention, the multivalent metal ion can be used such that it is included preferably in an amount of 0.01 to 20 wt %, more preferably 0.05 to 15 wt %, based on the dry weight of the sustained release composition of the present invention. If the content of the multivalent metal ion is below 0.01 wt % based on the dry weight of the sustained release composition, the sustained release effect may not be obtained, whereas if the content is greater than 20 wt %, there may be a problem of toxicity due to the metal ion.

The polymer complex containing active ingredient as formed is precipitated as particles in an aqueous solution.

The sustained release particulate composition containing polypeptide or the like according to the present invention is in the form of particle having uniform size of 5 to 250 μm, more concretely 50 to 150 μm.

In addition to the above-mentioned components, the sustained release composition of the present invention can further comprise pharmaceutical adjuvants such as preservative, stabilizing agent, wetting agent, or salts and/or buffering agent for controlling osmotic pressure, and other therapeutically useful substances. The sustained release composition containing protein, polypeptide or peptide drug according to the present invention can be dispersed in a pharmaceutically acceptable dispersion medium and then administered to human body. Examples of the dispersion medium can include distilled water for injection, 5% glucose, physiological saline, mineral oil, mono-, di- and triglyceride, etc.

In another aspect, the present invention provides a method for preparing a sustained release composition of protein, polypeptide or peptide drug, the method comprising the steps of: a) preparing an aqueous solution containing i) a protein, polypeptide or peptide as an active ingredient, and ii) the polylactic acid derivative compound of the chemical formula 1; and b) adding the aqueous solution of the above step a) dropwise to an aqueous solution comprising multivalent metal ion to obtain a precipitate.

Specifically, in step a) of the method for preparing the sustained release composition of the present invention, the active ingredient and the polylactic acid derivative compound of the chemical formula 2 can be added either at the same time or in the manner of a serial addition in which one component is first added and then other components are added. For example, the aqueous solution can be prepared by (a-1) dissolving the active ingredient and the polylactic acid derivative compound of the chemical formula 2 in water; or (a-2) first dissolving a polylactic acid derivative having carboxylic acids on both ends and an aqueous solution of alkali metal salt in water to prepare the polylactic acid derivative compound of the chemical formula 2, and then adding the active ingredient thereto; or (a-3) first dissolving a polylactic acid derivative compound having carboxylic acids on both ends and the active ingredient in water and then adding an aqueous solution of alkali metal salt thereto to prepare the aqueous solution containing the polylactic acid derivative compound of the chemical formula 2 and the active ingredient.

That is, the sustained release composition of the present invention can be prepared by using the polylactic acid derivative compound of the chemical formula 2 as the starting material (a-1), or alternatively by starting from the polylactic acid derivative compound having carboxylic acid on both ends and converting it into the polylactic acid derivative compound of the chemical formula 2 by means of the alkali metal salt, and then using the resulting compound in the subsequent steps (a-2 and a-3).

According to an embodiment of the method for preparing the sustained release composition of the present invention, the aqueous medium constituting said aqueous solution can be distilled water, or one or more buffer solutions selected from the group consisting of acetate, citrate, glycine, phosphate and carbonate salt buffer solutions. Protein, polypeptide or peptide drugs may sensitively respond to the composition of the formulation, particularly to its pH level, and accordingly their structures may be changed or their activity may decrease.

In step b) of the method for preparing the sustained release composition of the present invention, the aqueous solution obtained in step a) is slowly added dropwise to the aqueous solution containing the multivalent metal ion to form the precipitate. At this time, the active ingredient can be dispersed and precipitated in the inside of the complex formed from the polylactic acid derivative compound of the chemical formula 1 and the multivalent metal ion. In this step, the multivalent metal ion can be, for example, a multivalent ion of a metal selected from the group consisting of zinc, calcium, magnesium and iron. The multivalent metal ion can be provided, for example, in the form of salt compound such as chloride salts of those metals, but not particularly limited thereto. The concentration of multivalent ion in the aqueous solution can be 1 to 300 mg/ml, more particularly 1 to 100 mg/ml. In case where the polymer complex is formed, the multivalent metal ion forms the complex through either direct ionic bonding, or substitution of the alkali metal ion and then ionic bonding, to the anion in the polylactic acid derivative compound of the chemical formula 1. The active ingredient such as polypeptide is then entrapped within the complex, and the polymer complex containing the active ingredient formed as such is precipitated in the aqueous solution as microparticles. According to an embodiment of the present invention, the aqueous solution in step a) comprising the active ingredient and the polylactic acid derivative compound of the chemical formula 1 can be precipitated in step b) by adding to the aqueous solution of the multivalent metal ion of 1-30 times amount by volume ratio.

The method for preparing the sustained release composition of the present invention can further comprise, after step b), the step c) of centrifuging the precipitate obtained in step b) and then washing the precipitate with water. The step c) can be conducted in the manner that the precipitate obtained in step b) is centrifuged in a centrifuge maintained at low temperature, for example, 4° C. to separate the supernatant and the precipitate, and the separated precipitate is then washed with water.

In addition, the method for preparing the sustained release composition of the present invention can further comprise, after step c), the step d) of lyophilizing the precipitate separated in step c). In this step d), a lyophilizing adjuvant can be added during lyophilization procedure. The lyophilizing adjuvant can include sugars, sugar alcohols or a mixture thereof. Said sugar can be one or more selected from the group consisting of lactose, maltose, sucrose and trehalose, and said sugar alcohol can be one or more selected from the group consisting of mannitol, sorbitol, maltitol, xylitol and lactitol. In an embodiment of the present invention, the content of the lyophilizing adjuvant is 1 to 50 wt %, more preferably 1 to 30 wt %, based on the total dry weight of the lyophilized composition.

The sustained release microparticle composition according to the present invention can be prepared in the form of microparticle having uniform size of 5 to 250 μm, more preferably 50 to 150 μm, through electric sieve grinding or sonication optionally after step b), c) or d).

Since the method for preparing the sustained release composition of the present invention uses an aqueous solution without an organic solvent, no separation procedure for removing organic solvent is required and the denaturation of drug can be prevented during the production process, by which the pharmacological effect of drug can be maximized. In addition, the inclusion efficiency of protein, polypeptide or peptide drug is 90% or more, by which the loss of drug during the production process can be minimized.

When the sustained release composition according to the present invention is administered into the body, the polymer constituting the complex is decomposed in the body and accordingly the drug entrapped therein is released slowly. Prior to the present invention, polymers having a high molecular weight such as tens of thousand daltons had to be used for sustained release, i.e. for delaying the release time of drug. However, since the polymers having such a high molecular weight are not dissolved in water, it was required to use an organic solvent which may cause the denaturation of protein or peptide in the process for preparing a delivery carrier such as microparticle. However, since the sustained release microparticle composition according to the present invention uses a polymer having such a low molecular weight as being dissolved in water, an organic solvent is not necessarily used in preparing the sustained release composition. In addition, since the polymer can form the complex with multivalent metal ions, excellent effect of sustained release can be obtained when the sustained release composition of the present invention is administered into the body.

Hereinafter, the present invention will be illustrated more specifically through Preparation Examples, Examples and Experiments. However, they are provided to explain the present invention only, and the scope of the present invention is not limited thereto.

Preparation Example 1

Preparation of Polylactic Acid Derivative Compound 500 g (5.56 mole) of D,L-lactic acid and 18.9 g (0.16 mole) of succinic acid were introduced into a 1 L two-neck round bottom flask which was set up such that the reaction mixture could be stirred with a magnetic bar under nitrogen purge. An oil bath was heated to 160° C., and the reaction mixture was purged with nitrogen at a flow rate of 2000 mL/min. Water generated during the reaction was discharged out of the reactor along with the nitrogen flow. Water was removed for 1 hour, and the oil bath was heated to 200° C. The reaction was conducted for 24 hours and then terminated. Finally, 368 g of crude D,L-polylactic acid derivative having carboxylic acids on both ends was obtained. NMR spectrum of the prepared polylactic acid derivative is shown in FIG. 1. The result of measurement by the following NMR analysis showed that the number average molecular weight of the prepared polylactic acid derivative was 2,315 daltons.

<Number Average Molecular Weight Calculation from Peak Areas of $^1$H-NMR Scan>

$$\text{Number average molecular weight(daltons)} = \{(A+B)/(C/N)\} \times 72.1 \quad \text{[Equation 1]}$$

In the above equation 1,
A denotes the peak area of methylene proton of D,L-polylactic acid derivative,
B denotes the peak area of methylene proton of terminal D,L-lactic acid derivative of the polymer,
C denotes the peak area of methylene proton of dicarboxylic acid, and
N denotes the number of methylene protons in dicarboxylic acid.

Preparation Example 2

Preparation of Polylactic Acid Derivative

The polylactic acid derivative was polymerized according to the same method as described in Preparation Example 1, except that 39.3 g (0.33 mole) of succinic acid was used. Finally, 348 g of crude polylactic acid derivative having carboxylic acids on both ends was obtained. Its number average molecular weight measured by the above NMR analysis was 1,155 daltons.

Preparation Example 3

Purification of Polylactic Acid Derivative 100 g of the polylactic acid derivative obtained in Preparation Example 1 and 20 g of sodium bicarbonate (NaHCO$_3$) were introduced into a 2 L beaker, and 1 L of distilled water was added thereto. The mixture was heated to 60° C., and the polymer was dissolved for 1 hour under stirring. After dissolving the polymer, 1N aqueous solution of hydrogen chloride (HCl) was added dropwise to the aqueous polymer solution to precipitate the polymer. The precipitated polymer was filtered and washed with distilled water. The washing and filtering procedures were repeated 3 times to remove hydrogen chloride. The resulting polymer was lyophilized for 48 hours. Finally, 72.4 g of purified polylactic acid derivative having carboxylic acids on both ends was obtained and its number average molecular weight measured by the above NMR analysis was 2,703 daltons.

Preparation Example 4

Preparation of Polylactic Acid Derivative 381 g of the polylactic acid derivative having carboxylic acids on both ends was obtained according to the same method as described in Preparation Example 1, except that 21.1 g (0.16 mole) of glutaric acid was used instead of succinic acid. The number average molecular weight of the product measured by the above NMR analysis was 2,360 daltons.

Preparation Example 5

Preparation of Polylactic Acid Derivative 500 g (5.56 mole) of D,L-lactic acid was introduced into a 1 L two-neck round bottom flask which was set up such that the reactant could be stirred with a magnetic bar under nitrogen purge. An oil bath was heated to 160° C., and the reactant was purged with nitrogen at a flow rate of 2000 mL/min. Water generated during the reaction was discharged out of the reactor along with the nitrogen flow. Water was removed for 1 hour, and the oil bath was heated to 200° C. The reaction was conducted for 24 hours and then terminated. Finally, a crude D,L-polylactic acid having hydroxyl group and carboxylic acid on two ends, respectively, was obtained. To the resulting product, 35 g (0.35 mole) of succinic anhydride was added and the mixture was heated at 120° C. for 6 hours to allow the reaction with the hydroxyl group on one end of the polylactic acid. The prepared polylactic acid derivative had the number average molecular weight of 2,240 daltons, as measured by the above NMR analysis.

Example 1

Preparation of Sodium Salt of Polylactic Acid Derivative 100 g of the polylactic acid derivative obtained in Preparation Example 1 was added to, and dissolved in, 150 mL of acetonitrile. 150 mL of an aqueous solution of sodium bicarbonate (0.1 g/mL) was slowly added thereto. The reaction mixture was stirred for 2 hours at room temperature to neutralize the polymer, thereby preparing sodium salt of polylactic acid derivative.

After the above, the prepared polymer was purified by the salting-out method. That is, 15 g of sodium chloride (NaCl) was added to the resulting reaction solution under stirring and dissolved therein, and the phases were then separated for 2 hours in a separation funnel and the aqueous layer was removed.

100 mL of distilled water and 10 g of sodium chloride were again added to, and dissolved in, the polymer solution obtained as the organic layer, and the phases were then separated again by using the separation funnel and the aqueous layer was removed. The organic layer solution comprising the obtained polymer was subjected to a rotary fractional distillation at 50° C. to completely remove the organic solvent and a small amount of distilled water.

After the removal of organic solvent and distilled water, the obtained polymer was dissolved by adding 500 mL of anhydrous acetone thereto, and the remaining precipitate was filtered and removed by using a filter paper. The filtered polymer solution was subjected to the rotary fractional distillation for 2 hours at 50° C. to completely remove acetone.

Figure 2:
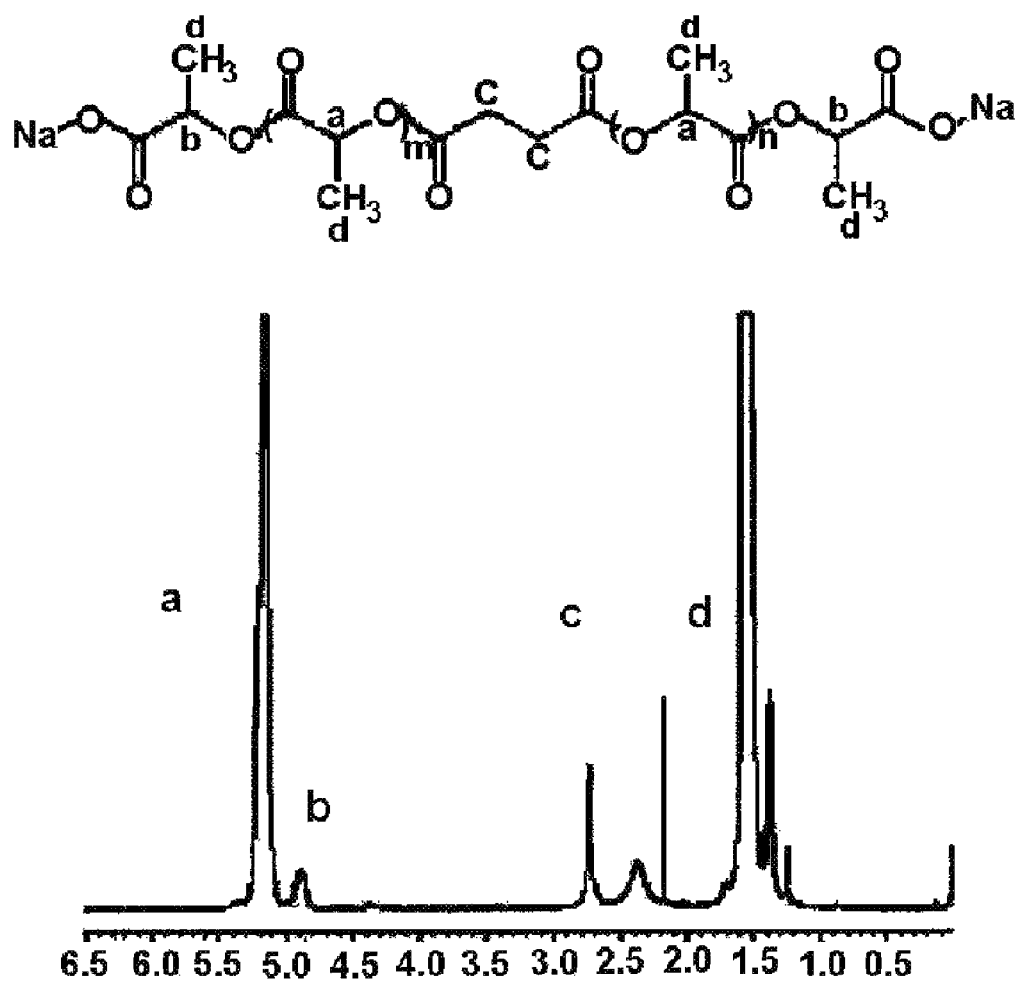
FIG. 2 is a $^1$H-NMR spectrum obtained from the sodium salt of the polylactic acid derivative of the chemical formula 1 prepared in Example 1, dissolved in CDCl$_3$.

After the removal of acetone, the obtained polymer was dried under vacuum in a vacuum oven at 50° C. for 3 days. Finally, 91 g of purified sodium salt of polylactic acid derivative having carboxylic acid-sodium salts on both ends was obtained. NMR spectrum of the prepared salt of polylactic acid derivative is shown in FIG. 2. It s number average molecular weight measured by the above NMR analysis was 2,178 daltons.

Example 2

Preparation of Sodium Salt of Polylactic Acid Derivative 93 g of purified salt of polylactic acid derivative having carboxylic acid-sodium salts on both ends was obtained by using 100 g of the polylactic acid derivative obtained in Preparation Example 2, according to the same method as described in Example 1. Its number average molecular weight measured by the above NMR analysis was 1,125 daltons.

Example 3

Preparation of Sodium Salt of Polylactic Acid Derivative 91 g of purified salt of polylactic acid derivative having carboxylic acid-sodium salts on both ends was obtained by using 100 g of the polylactic acid derivative obtained in Preparation Example 4, according to the same method as described in Example 1. Its number average molecular weight measured by the above NMR analysis was 2,250 daltons.

Example 4

Preparation of Sodium Salt of Polylactic Acid Derivative 90 g of purified salt of polylactic acid derivative having carboxylic acid-sodium salts on both ends was obtained by using 100 g of the polylactic acid derivative obtained in Preparation Example 5, according to the same method as described in Example 1. Its number average molecular weight measured by the above NMR analysis was 2,080 daltons.

Example 5

Preparation of Sustained Release Composition Containing Human Growth Hormone (hGH)

4.5 g of the sodium salt of polylactic acid derivative prepared in Example 1 and 500 mg of human growth hormone (3.0 IU/mg) were dissolved in 20 mL of water to prepare an aqueous hGH-polymer solution.

250 mL of an aqueous solution of zinc chloride ($ZnCl_2$) as the multivalent metal salt (50 mg/mL) was prepared. To this solution, the aqueous hGH-polymer solution was added dropwise to form precipitate of the composition containing human growth hormone. The resulting mixture was centrifuged at 3,500 rpm for 10 minutes by using a centrifuge maintained at 4° C. to separate the supernatant and the precipitate.

The precipitate was filtered and washed two times with 500 mL of distilled water, and then lyophilized. The lyophilized composition was screened by using 100 to 400 mesh sieve to obtain the microparticle composition of 50 to 150 μm.

Human growth hormone in the lyophilized microparticle composition as obtained was quantified by using the following BCA assay (Micro BCA Protein Assay Kit, Thermo Scientific). The hGH content and inclusion efficiency resulting from the quantitative analysis were 9.54 wt % and 92.6%, respectively.

<Protein Content and Inclusion Efficiency Measurement Using BCA Assay (Micro BCA Protein Assay Kit, Thermo Scientific)>

(1) Protein Content Measurement $$\text{Content (\%)} = \frac{\text{Amount of peptide or protein entrapped in microparticle (g)}}{\text{Total amount of microparticle composition (g)}} \times 100 \qquad \text{[Equation 2]}$$

(2) Protein Inclusion Efficiency Measurement $$\text{Inclusion efficiency (\%)} = \frac{\text{Amount of peptide or protein entrapped in microparticle (g)}}{\text{Amount used in preparing microparticle composition (g))}} \times 100 \qquad \text{[Equation 3]}$$

Example 6

Preparation of Sustained Release Composition Containing Human Growth Hormone The microparticle composition containing human growth hormone was prepared according to the same method as described in Example 5, except that 4.75 g of the polylactic acid derivative sodium salt prepared in Example 1 and 250 mg of human growth hormone (3.0 IU/mg) were used. Human growth hormone in the prepared composition was quantified by the above BCA assay, and the hGH content and inclusion efficiency were 4.72 wt % and 91.7%, respectively.

Example 7

Preparation of Sustained Release Composition Containing Human Growth Hormone The microparticle composition containing human growth hormone was prepared according to the same method as described in Example 5, except that 4.75 g of the polylactic acid derivative sodium salt prepared in Example 1 and 100 mg of human growth hormone (3.0 IU/mg) were used. Human growth hormone in the prepared composition was quantified by the above BCA assay, and the hGH content and inclusion efficiency were 1.93 wt % and 93.7%, respectively.

Example 8

Preparation of Sustained Release Composition Containing Human Growth Hormone The microparticle composition containing human growth hormone was prepared according to the same method as described in Example 6, except that the polylactic acid derivative sodium salt prepared in Example 2 was used. Human growth hormone in the prepared composition was quantified by the above BCA assay, and the hGH content and inclusion efficiency were 4.72 wt % and 91.7%, respectively.

Example 9

Preparation of Sustained Release Composition Containing Human Growth Hormone 4.9 g of the polylactic acid derivative sodium salt purified in Preparation Example 3 and 100 mg of human growth hormone (3.0 μl/mg) were dissolved in 20 mL of water, and then 0.3 g of sodium bicarbonate ($NaHCO_3$) was added thereto to prepare an aqueous hGH-polymer solution.

250 mL of an aqueous solution of zinc chloride ($ZnCl_2$) as the multivalent metal salt (50 mg/mL) was prepared. To this solution, the aqueous hGH-polymer solution was added dropwise to form precipitate of the composition containing human growth hormone. The resulting mixture was centrifuged at 3,500 rpm for 10 minutes by using a centrifuge maintained at 4° C. to separate the supernatant and the precipitate.

The precipitate was filtered and washed two times with 500 mL of distilled water, and then lyophilized. The lyophilized composition was screened by using 100 to 400 mesh sieve to obtain the microparticle composition of 50 to 150 μm.

Human growth hormone in the lyophilized microparticle composition as obtained was quantified by the above BCA assay, and the hGH content and inclusion efficiency were 4.86 wt % and 94.4%, respectively.

Example 10

Preparation of Sustained Release Composition Containing Erythropoietin (EPO)

1 g of the polylactic acid derivative sodium salt prepared in Example 1 and 0.4 mg of erythropoietin (EPO) (41 IU/mg) were dissolved in 5 mL of water to prepare an aqueous EPO-polymer solution.

5.5 mL of an aqueous solution of zinc chloride ($ZnCl_2$) as the multivalent metal salt (12.5 mg/mL) was prepared. To this solution, the aqueous EPO-polymer solution was added with stirring to form precipitate of the composition containing erythropoietin. The resulting mixture was centrifuged at 3,500 rpm for 10 minutes by using a centrifuge maintained at 4° C. to separate the supernatant and the precipitate.

The supernatant was completely removed and the obtained precipitate was lyophilized. The lyophilized composition was screened by using 100 to 400 mesh sieve to obtain the microparticle composition of 50 to 150 μm.

Erythropoietin in the lyophilized microparticle composition as obtained was quantified by the above BCA assay, and the erythropoietin content and inclusion efficiency were 0.038 wt % and 92.2%, respectively.

Example 11

Preparation of Sustained Release Composition Containing Exenatide 4.9 g of the polylactic acid derivative sodium salt prepared in Example 1 and 100 mg of exenatide were dissolved in 45 mL of water to prepare an aqueous solution, and the solution was filtered by using a 0.45 pun filter to remove impurities.

500 mL of an aqueous solution of zinc chloride ($ZnCl_2$) as the multivalent metal salt (25 mg/mL) was prepared. To this solution, the aqueous exenatide-polymer solution was added dropwise at the rate of 3 mL/min with stirring at the rate of 120 rpm to form precipitate of the composition containing exenatide.

The precipitate was filtered and washed two times with 500 mL of distilled water, and then dried under vacuum for 1 day at room temperature. The dried composition was ground with a grinder, screened by using 100 to 400 mesh sieve to obtain the microparticle composition of 50 to 150 μm.

Exenatide in the dried microparticle composition as obtained was quantified by the above BCA assay, and the exenatide content and inclusion efficiency were 1.97 wt % and 95.6%, respectively.

Example 12

Preparation of Sustained Release Composition Containing Exenatide

The microparticle composition containing exenatide was prepared according to the same method as described in Example 11, except that calcium chloride ($CaCl_2$) was used instead of zinc chloride ($ZnCl_2$) as the multivalent metal salt. Exenatide in the dried microparticle composition as obtained was quantified by the above BCA assay, and the exenatide content and inclusion efficiency were 1.92 wt % and 93.2%, respectively.

Example 13

Preparation of Sustained Release Composition Containing Exenatide

The microparticle composition containing exenatide was prepared according to the same method as described in Example 11, except that 4.9 g of the polylactic acid derivative sodium salt prepared in Example 3 was used. Exenatide in the dried microparticle composition as obtained was quantified by the above BCA assay, and the exenatide content and inclusion efficiency were 1.94 wt % and 94.2%, respectively.

Comparative Example 1

Preparation of Aqueous Solution Composition of Human Growth Hormone (hGH)

An aqueous solution of human growth hormone was prepared by dissolving the components listed in the following Table 1 in 10 mL of water for injection.

TABLE 1

| | |
|---|---|
| hGH | 0.1 g |
| Glycine | 1.0 g |
| Mannitol | 0.1 g |
| Lactose | 0.1 g |
| Sodium bicarbonate | 0.1 g |

Comparative Example 2

Preparation of Aqueous Solution Composition of Erythropoietin (EPO)

An aqueous solution of erythropoietin was prepared by dissolving the components listed in the following Table 2 in 1.0 mL of water for injection.

TABLE 2

| | |
|---|---|
| EPO | 4,100 IU (0.1 g) |
| Human serum albumin | 5 mg |
| Sodium chloride | 10 mg |
| Monobasic sodium phosphate dihydrate | 5 mg |
| Dibasic sodium phosphate dihydrate | 2 mg |

Experiment 1

Pharmacokinetic Test of Composition Containing Human Growth Hormone (hGH)

The compositions containing human growth hormone (hGH) as prepared in Examples 5 to 9 and Comparative Example 1 were tested for their pharmacokinetic properties.

S.D. rats (190±20 g, 5 to 6 weeks old) provided from Charles River Laboratories (Orient, Korea) were accommodated for one week or more in a breeding room maintained at constant temperature and constant humidity. Upon observing the general conditions, healthy animals by all appearance were selected and used for the experiment. The experimental animals were bred under the conditions including artificial illumination at an interval of 12 hours, illuminance of 300 to 500 Lux, temperature of 23±11° C., and relative humidity of 65±10%, and allowed to freely take sterilized solid feed and tap water.

Figure 3:
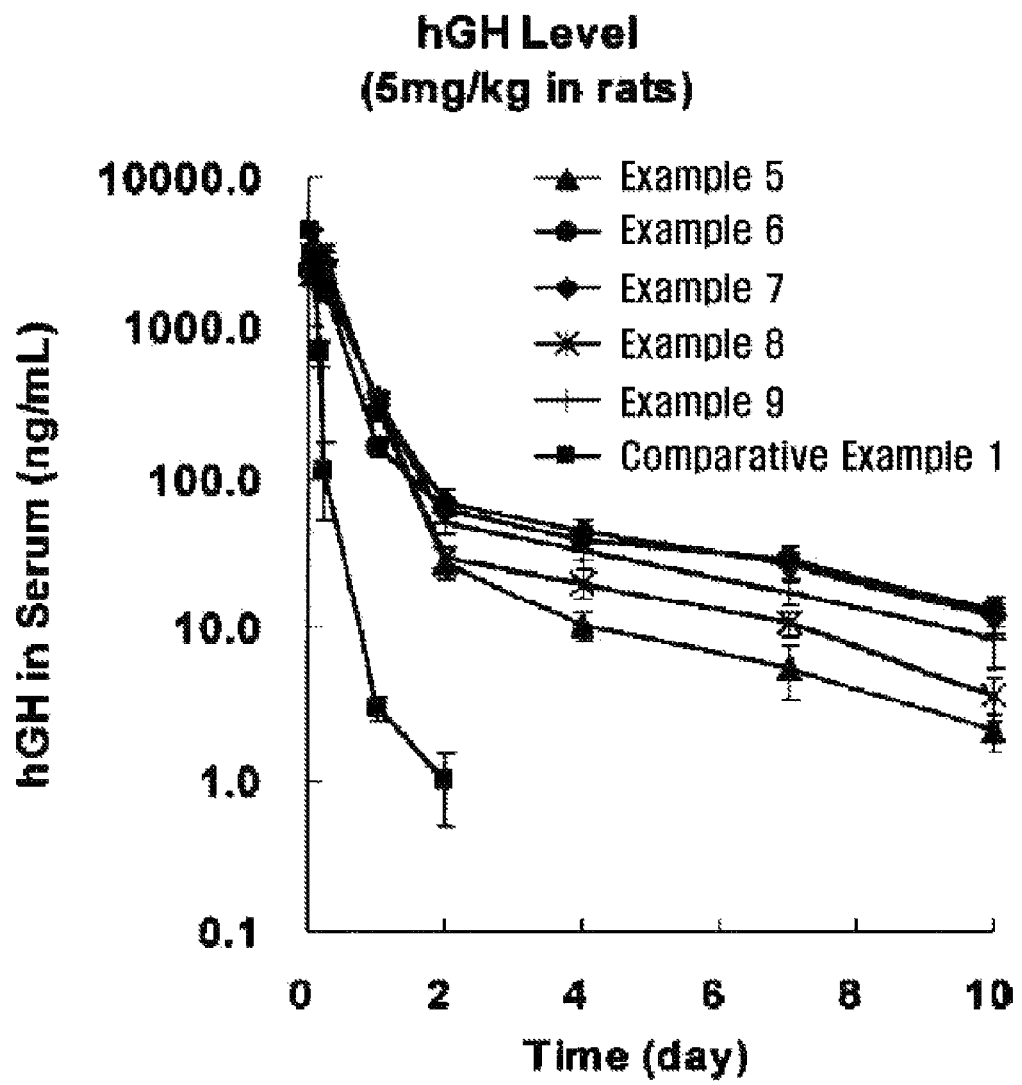
FIG. 3 is a graph obtained from Experiment 1, showing the pharmacokinetic test results for the formulation containing human growth hormone in rats.

Each of the compositions was subcutaneously injected into rats (n=5) at a dose of 5 mg/kg, and then blood was collected for 10 days at a regular interval and quantified for hGH level in blood by means of Quantikine hGH immunoassay kit (R&D Systems). The quantification results are shown in FIG. 3. As shown in FIG. 3, the composition containing human growth hormone according to the present invention maintained 1 ng/mL or higher of the human growth hormone level in blood for 10 days or longer. Furthermore, the observation result of autopsy showed no toxicity caused by the composition of the present invention.

Experiment 2

Efficacy Test of Composition Containing Human Growth Hormone

The compositions containing human growth hormone (hGH) as prepared in Examples 5 to 6 and Comparative Example 1 were administered to rats (hypophysectomized rats)—from which pituitary gland was extracted to cause a deficiency of growth hormone—to perform the efficacy test.

As the disease model animal, hypophysectomized S.D. rats (90±10 g, 4 weeks old, Japan SLC, Inc.) were accommodated for one week or more in a breeding room maintained at constant temperature and constant humidity. Upon observing the general conditions, healthy animals by all appearance and having no weight change were selected and used for the experiment. The experimental animals were bred under the conditions including artificial illumination at an interval of 12 hours, illuminance of 300 to 500 Lux, temperature of 23±1° C., and relative humidity of 65±10%, and allowed to freely take sterilized solid feed and tap water.

The compositions of Examples 5 and 6 were subcutaneously injected one time at a dose of 5 mg/kg, and the composition of Comparative Example 1 was subcutaneously injected once per day at a dose of 0.71 mg/kg for 7 days (n=6). Blood was collected at a regular interval to quantify IGF-1 (Insulin Like Growth Factor-1) level in blood by means of Quantikine IGF-1 immunoassay kit (R&D Systems). Furthermore, the weights of experimental animals were measured to record a change in weight. The result of quantification and weight measurement are shown in FIGS. 4 and 5.

Figure 4:
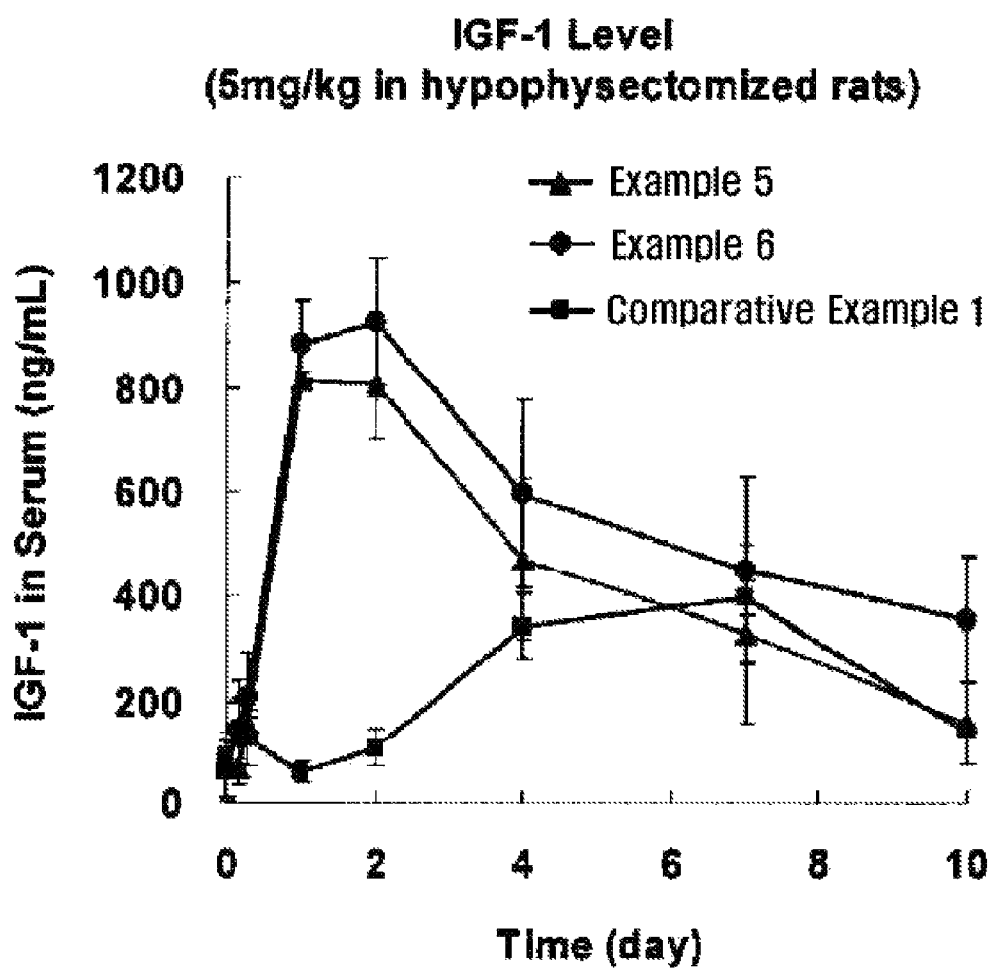
FIG. 4 is a graph obtained from Experiment 2, showing the measurement results of IGF-1 concentration in blood generated after subcutaneously injecting the formulation containing human growth hormone into rats, pituitary gland of which was removed.

As shown in FIG. 4, with respect to level of IGF-1 in blood produced by growth hormone, a single administration of the composition of the present invention exhibits better result, as compared with the administration of the existing, commercially available formulation once per day for 7 days.

Figure 5:
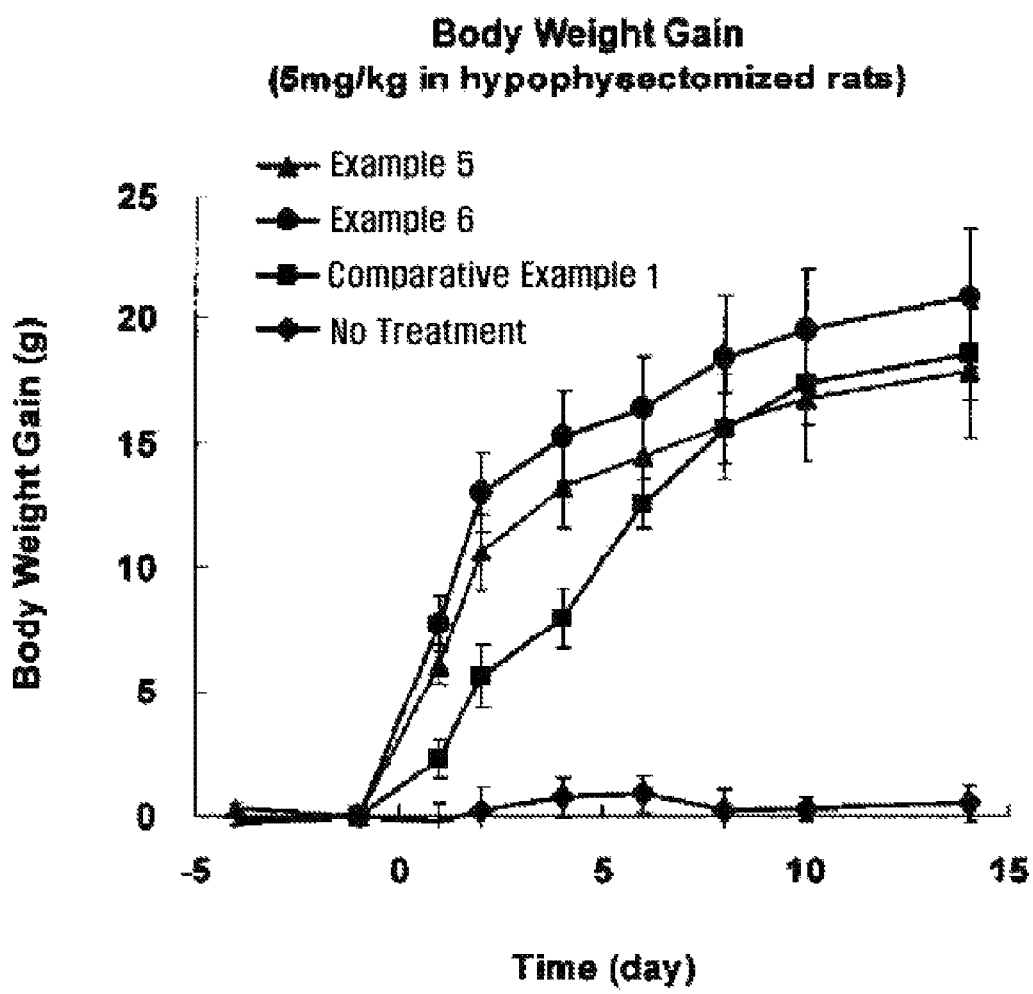
FIG. 5 is a graph obtained from Experiment 2, showing the measurement results of weight gain after subcutaneously injecting the formulation containing human growth hormone into rats, pituitary gland of which was removed.

In addition, as shown in FIG. 5, when the composition of the present invention was administered one time, the weight increased by about 20% after 2 weeks, and thus the composition of the present invention exhibits better result, as compared with the administration of the existing, commercially available formulation once per day for 7 days. The negative control group (no treatment) to which growth hormone was not administered did not show weight gain. The observation result of autopsy showed no toxicity caused by the composition of the present invention.

Experiment 3

Pharmacokinetic Test of Composition Containing Erythropoietin (EPO)

The compositions containing erythropoietin as prepared in Example 10 and Comparative Example 2 were tested for their pharmacokinetic properties.

S.D. rats (190±20 g, 5 to 6 weeks old) were provided from Charles River Laboratories (Orient, Korea), and managed under the same conditions as in Experiment 1.

Figure 6:
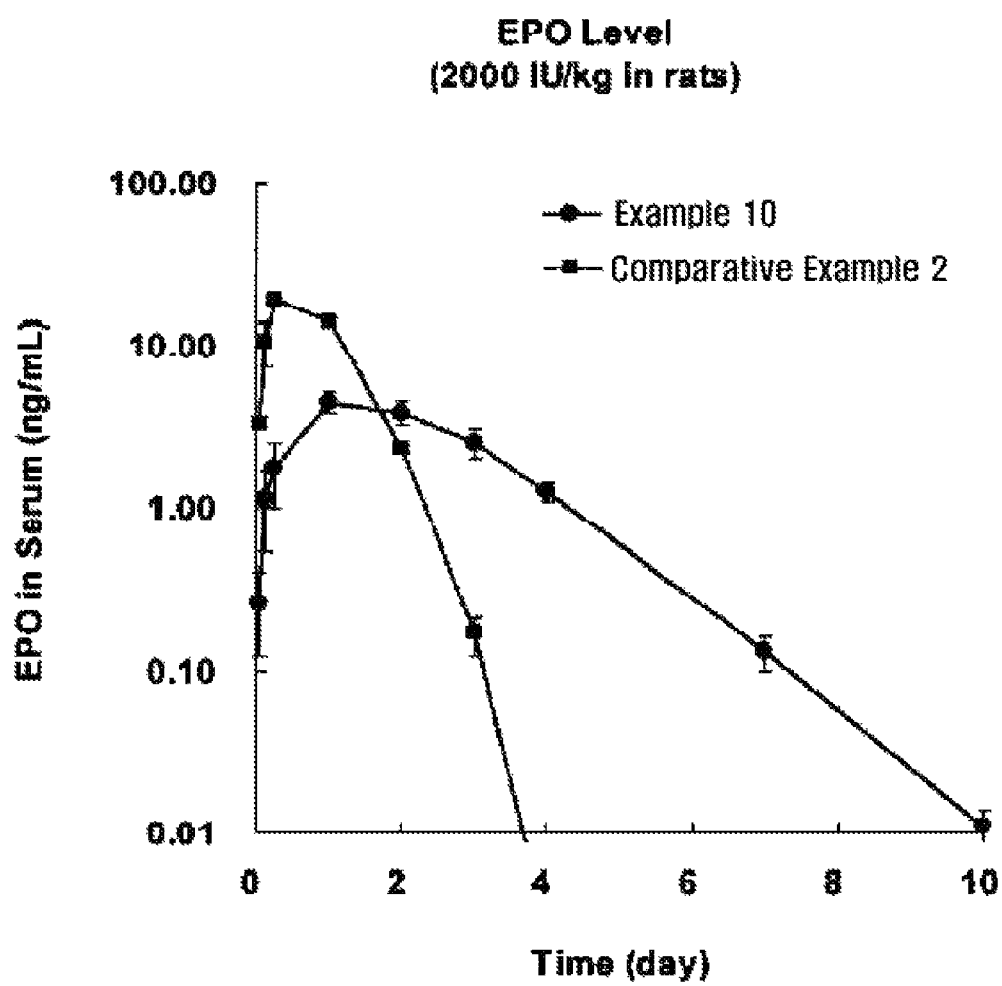
FIG. 6 is a graph obtained from Experiment 3, showing the pharmacokinetic test results for the formulation containing erythropoietin in rats.

Each of the compositions was subcutaneously injected into rats (n=6) at a dose of 2000 IU/kg, and then blood was collected at a regular interval and quantified for erythropoietin level in blood by means of Enzyme immunoassay kit (DEP00, R&D systems). The quantification results are shown in FIG. 6. As shown in FIG. 6, the composition containing erythropoietin according to the present invention prolonged the time to maintain the blood level and exhibited the sustained release effect for one week, as compared with the commercially available composition for daily administration. Furthermore, the observation result of autopsy showed no toxicity caused by the composition of the present invention.

Experiment 4

Pharmacokinetic Test of Composition Containing Exenatide

The compositions containing exenatide as prepared in Examples 11 to 13 were tested for their pharmacokinetic properties.

S.D. rats (190±20 g, 5 to 6 weeks old) were provided from Charles River Laboratories (Orient, Korea), and managed under the same conditions as in Experiment 1.

Figure 7:
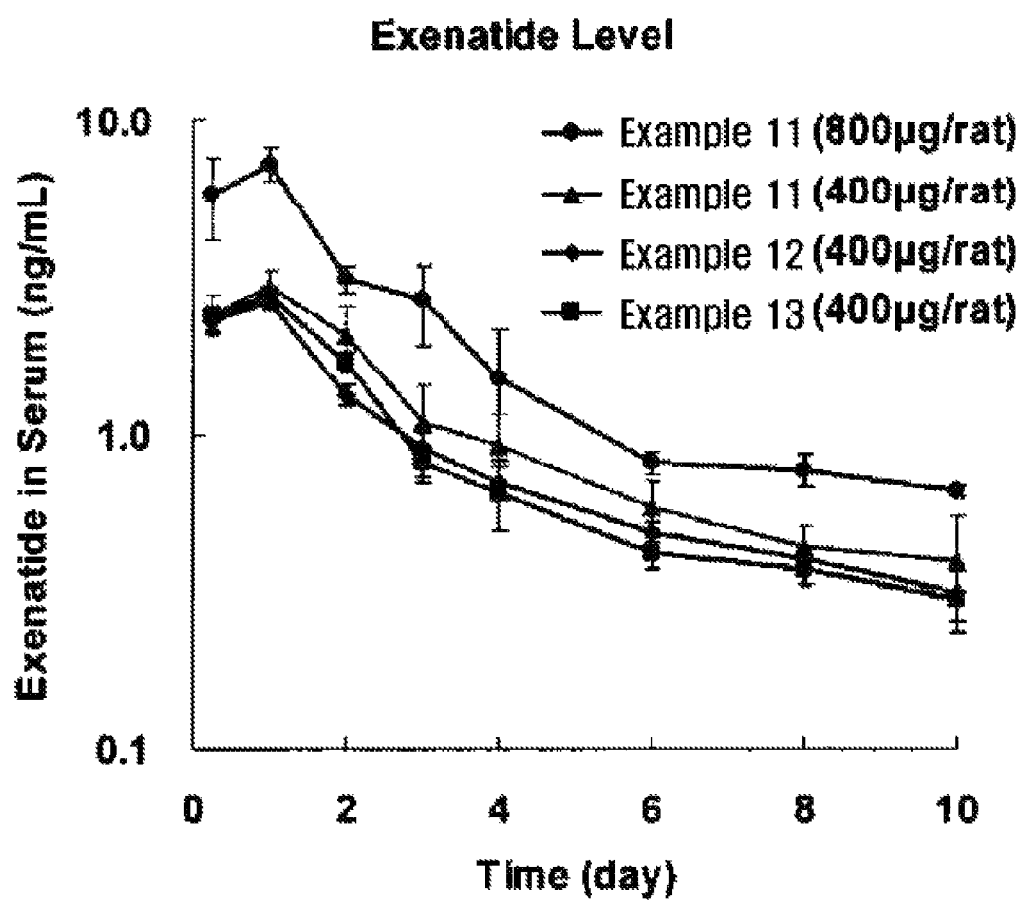
FIG. 7 is a graph obtained from Experiment 4, showing the pharmacokinetic test results for the formulation containing exenatide in rats.

The composition of Example 11 (400 μg/rat, 800 μg/rat) and the compositions of Examples 12 and 13 (400 μg/rat) were subcutaneously injected into rats (n=6), and then blood was collected at a regular interval and quantified for exenatide level in blood by means of Enzyme immunoassay kit (EK-070-94, Phoenix Pharmaceuticals, Inc.). The quantification results are shown in FIG. 7. As shown in FIG. 7, the composition containing exenatide according to the present invention maintained 0.1 ng/mL or more of the blood level for one week by a single administration. The observation result of autopsy showed no toxicity caused by the composition of the present invention.

The invention claimed is:

1. A sustained release microparticle composition of protein, polypeptide or peptide drug, consisting of:
   i) a protein, polypeptide or peptide as an active ingredient, and
   ii) a complex of a water-soluble ionic polymer of the following chemical formula 6 having a number average molecular weight of 1,000 to 4,000 daltons with a multivalent metal ion, as a drug delivery carrier;

Chemical Formula 6

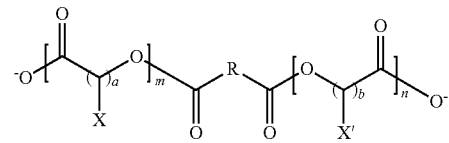

wherein
X and X' are independently hydrogen, alkyl or aryl,
m and n are independently an integer of 0 to 95, provided that 5<m+n<100,
a and b are independently an integer of 1 to 6,
R is unsubstituted or substituted —$(CH_2)_k$— where k is an integer of 0 to 10, a divalent alkenyl having 2 to 10 carbon atoms, a divalent aryl having 6 to 20 carbon atoms, or a combination thereof;
wherein said active ingredient is entrapped within the complex.

2. The sustained release microparticle composition according to claim 1, which contains said active ingredient in an amount of 0.01 to 60 wt %, based on the dry weight of the composition.

3. The sustained release microparticle composition according to claim 1, which contains said drug delivery carrier in an amount of 39.9 to 99.9 wt %, based on the dry weight of the composition.

4. The sustained release microparticle composition according to claim 1, wherein said active ingredient is growth hormone, erythropoietin, monoclonal antibody, granulocyte colony stimulating factor, macrophage colony stimulating factor, granulocyte-macrophage colony stimulating factor, thrombopoietin, insulin-like growth factor, epithelial growth factor, platelet-derived growth factor, fibroblast growth factor, transforming growth factor, interferon, interleukin, tumor necrosis factor, streptokinase, urokinase, staphylokinase, DNAse, glucocerebrosidase, alpha galactosidase, exenatide, octreotide, insulin, glucagon, luteinizing hormone releasing hormone, goserelin, leuprorelin, follicle stimulating factor, thyroid stimulating hormone, fertirelin, calcitonin, corticotropin releasing factor, brain natriuretic peptide, thymopentin, corticotropin, elcatonin, beta amyloid, triptorelin, buserelin, thymosin, somatostatin, alarelin, angiotensin, argipressin, atosiban, bivalirudin, cetrorelix, deslorelin, desmopressin, elcatonin, enfuvirtide, eptifibatide, GLP-1, gonandorelin, lyspressin, nafarelin, nesiritide, oxytocin, pramlintide, secretin, teriparatide, terlipressin, tetracosactide, vapreotide, or a mixture thereof.

5. A sustained release microparticle composition of protein, polypeptide or peptide drug, consisting of:
  i) a protein, polypeptide or peptide as an active ingredient;
  ii) a complex of a water-soluble ionic polymer of the following chemical formula 6 having a number average molecular weight of 1,000 to 4,000 daltons with a multivalent metal ion, as a drug delivery carrier:

[Chemical Formula 6]

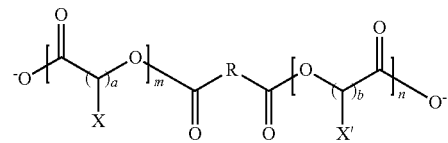

wherein

X and X' are independently hydrogen, alkyl or aryl, m and n are independently an integer of 0 to 95, provided that 5<m+n<100, a and b are independently an integer of 1 to 6, R is unsubstituted or substituted —$(CH_2)_k$— where k is an integer of 0 to 10, a divalent alkenyl having 2 to 10 carbon atoms, a divalent aryl having 6 to 20 carbon atoms, or a combination thereof; and iii) a lyophilizing adjuvant, wherein said active ingredient is entrapped within the complex.

* * * * *